United States Patent [19]

Rolf et al.

[11] 4,260,540
[45] Apr. 7, 1981

[54] AZO DYE PIGMENTS CONTAINING 4-QUINAZOLINONE MOIETIES

[75] Inventors: Meinhard Rolf; Rütger Neeff; Walter Müller, all of Leverkusen, Fed. Rep. of Germany

[73] Assignee: Bayer Aktiengesellschaft, Leverkusen, Fed. Rep. of Germany

[21] Appl. No.: 22,295

[22] Filed: Mar. 20, 1979

Related U.S. Application Data

[63] Continuation-in-part of Ser. No. 837,404, Sep. 28, 1977.

[30] Foreign Application Priority Data

Mar. 22, 1978 [DE] Fed. Rep. of Germany ....... 2812635

[51] Int. Cl.³ ............ C09K 17/00; C09B 29/22; C09B 29/36; C09B 62/08
[52] U.S. Cl. ............... 260/42.21; 260/154; 260/37 R; 260/37 N; 260/37 P; 260/37 NP
[58] Field of Search ............... 260/154, 42.21; 106/288 Q, 300, 308 Q, 308 N, 309; 427/407 R; 428/411, 413, 423, 474, 480, 500, 538

[56] References Cited

U.S. PATENT DOCUMENTS

| | | | |
|---|---|---|---|
| 1,032,734 | 7/1912 | Bogert | 260/154 |
| 3,382,228 | 5/1968 | Ferrari et al. | 260/158 |
| 3,923,774 | 12/1975 | Dimroth | 260/154 |

FOREIGN PATENT DOCUMENTS 2245093 3/1974 Fed. Rep. of Germany .......... 260/154
48-30655 9/1973 Japan ................................. 544/284

*Primary Examiner*—John F. Niebling
*Attorney, Agent, or Firm*—Sprung, Felfe, Horn, Lynch & Kramer

[57] ABSTRACT

Heterocyclic compounds of the formula

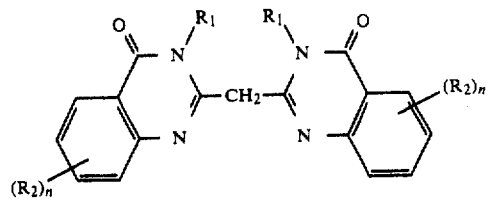

wherein
$R_1$ denotes hydrogen or $C_1-C_4$-alkyl or the two $R_1$s together denote CO,
$R_2$ denotes a substituent and
n denotes 0, 1, 2, 3 or 4, processes for their preparation, azo pigments prepared therefrom by a coupling reaction with a diazo component of an aromatic or hetero-aromatic amine free from sulphonic acid groups, and the use of these azo pigments for pigmenting organic macromolecular materials and especially in the spin dyeing of polyacrylonitrile.

6 Claims, No Drawings

AZO DYE PIGMENTS CONTAINING 4-QUINAZOLINONE MOIETIES

This is a continuation-in-part of copending application Ser. No. 837,404, filed Sept. 28, 1977, entitled "Heterocyclic Dyes and Pigments Containing 4-Quinazolinone Moieties."

The invention relates to heterocyclic compounds of the formula $$(I)$$

processes for their preparation and their use as coupling components for azo dyestuffs and to the azo pigments prepared therefrom.

In the formula I,
$R_1$ denotes hydrogen or $C_1$-$C_4$ alkyl, especially methyl, or the two $R_1$s together denote CO,
$R_2$ denotes a substituent and
n denotes 0, 1, 2, 3 or 4.

Suitable substituents $R_2$ are, for example, halogen, such as chlorine and bromine, $C_1$-$C_4$-alkyl, $C_1$-$C_4$-alkoxy, nitro, trifluoromethyl, cyano, optionally substituted carboxamide and sulphonamide, acylamino or arylamino.

Possible substituents of the carboxamide and sulphonamide groups are $C_1$-$C_4$-alkyl, and phenyl and benzyl which are optionally substituted by $C_1$-$C_4$-alkyl, $C_1$-$C_4$-alkoxy, fluorine, chlorine, bromine or nitro. Acyl groups which may be mentioned are, in particular, $C_1$-$C_4$-alkylcarbonyl and benzoyl which is optionally substituted in the benzene nucleus by chlorine, $C_1$-$C_4$-alkyl, $C_1$-$C_4$-alkoxy or nitro. Arylamino is, in particular, phenylamino which is optionally substituted by $C_1$-$C_4$-alkyl, $C_1$-$C_4$-alkoxy, fluorine, chlorine, bromine or nitro.

The compounds of the formula I are obtained by reacting functional derivatives of malonic acid with anthranilic acid amides of the formula $$(II)$$

wherein
$R_1$, $R_2$ and n have the abovementioned meaning.

The malonic acid derivative and the anthranilic acid amide are reacted in a molar ratio of 1:2 and in general the anthranilic acid amide is employed in a 0.1 to 10-fold excess. The reaction is carried out at 120° to 220° C. without a solvent or in an inert organic solvent such as o-dichlorobenzene, 1,2,4-trichlorobenzene, ethylene glycol dimethyl ether, ethylene glycol diethyl ether, xylene or nitrobenzene, if appropriate in the presence of catalytic amounts (0.001 to 0.1 mol per mol of malonic acid derivative) of organic bases such as pyridine, quinoline, triethylamine, N,N-dimethylaniline, N,N-dimethylbenzylamine, N-methylmorpholine or diazabicyclooctane.

Malonic acid derivatives which can be used are, in particular, the malonic acid halides, in particular malonic acid dichloride, malonic acid dialkyl esters, in particular the dimethyl and diethyl esters, malonic acid iminoalkyl esters, especially the dimethyl and diethyl esters, and also malodinitrile.

The anthranilic acid amides of the formula II are obtained by reacting the corresponding isatoic anhydrides of the formula $$(III)$$

wherein
$R_2$ and n have the abovementioned meaning,
with amines of the formula $$R_1-NH_2 \quad (IV)$$

wherein
$R_1$ has the abovementioned meaning.

The compounds of the formula I are high-melting, pale yellow compounds which are sparingly soluble in organic solvents. They are suitable as coupling components for the preparation of azo dyestuffs and in particular for the preparation of azo pigments.

The compound in which $R_1$ is hydrogen and n is 0 is particularly preferred.

The invention therefore also relates to azo pigments of the formula $$(V)$$

wherein
D denotes the radical of an aromatic or heteroaromatic amine free from sulphonic acid groups and
m denotes an integer, preferably 1 or 2, and
$R_1$, $R_2$ and n have the abovementioned meaning.

Suitable diazo components are, for example, aniline, 2-methylaniline, 2,4-dimethylaniline, 2-nitroaniline, 3-nitroaniline, 4-nitroaniline, 2,4-dinitroaniline, 2-chloro-4-nitroaniline, 4-chloro-2-nitroaniline, 2-chloro-5-nitroaniline, 2-nitro-4-methylaniline, 2-methyl-4-nitroaniline, 2-methyl-5-nitroaniline, 4-methoxy-2-nitroaniline, 2-cyano-4-nitroaniline, 2-bromo-4-nitroaniline, 2-nitro-4-methylsulphonylaniline, 2-nitro-4-ethylsulphonylaniline, 2-chloroaniline, 4-chloroaniline, 2,4-dichloroaniline, 2,5-dichloroaniline, 2,6-dichloroaniline, 3,4-dichloroaniline, 3,5-dichloroaniline, 2,4,5-trichloroaniline, 2,4,6-trichloroaniline, 2-cyano-5-chloroaniline, 2-methyl-4-chloroaniline, 2-methyl-5-chloroaniline, 2,4-dichloro-5-ethylaniline, 2,5-dichloro-4-methylaniline, 2-chloro-4-methylsulphonylaniline, 2-cyano-4-nitroaniline, 2,4-dichloro-5-methoxyaniline, 2-trifluoromethyl-aniline, 2-chloro-5-trifluoromethylaniline, 4-chloro-2-trifluoromethylaniline, 3,5-bis-trifluoromethylaniline, 2,4-dimethoxy-aniline, 2,5-dimethoxyaniline, 2,5-diethoxyaniline, 2,4-dimethoxy-5-chloroaniline, 2,5-dimethoxy-4-chloroaniline, 2-methoxy-5-methylaniline, 4-methoxy-2-methylaniline, 2-methoxy-5-methyl-4-chloroaniline, 2-methoxy-4-nitroaniline, 4-methoxy-2-nitroaniline, 2-methoxy-5-nitroaniline, 2,5-dimethoxy-4-nitroaniline, 2-methoxy-5-methyl-4-nitroaniline, 2-methoxy-5-chloro-4-nitroaniline, 2-methoxy-5-ethylsulphonylaniline, 2-methoxy-5-phenylsulphonylaniline, 2-methoxy-5-benzylsulphonylaniline, 2-methoxy-4-chloroaniline, 2-ethoxy-4-chloroaniline, 2-methoxy-5-chloroaniline, 2-ethoxy-5-chloroaniline, 2-methoxy-4,5-dichloroaniline, 2-amino-5-chloro-diphenyl ether, 2-amino-4,4'-dichlorodiphenyl ether, 2-amino-4,6-dichlorodiphenyl ether, 4-nitrophenyl 4-amino-5-methoxybenzenesulphonate, 5-acetylamino-2-nitroaniline, 5-acetylamino-2-chloro-5-methylaniline, 4-acetylamino-2,5-dichloroaniline, 5-acetylamino-2,4-dichloroaniline, 4-benzoylamino-2-methyl-5-methoxyaniline, 5-benzoylamino-2-chloroaniline, 4-benzoylamino-2-chloro-5-methoxyaniline, 2-aminobenzoic acid, methyl 2-aminobenzoate, ethyl 2-aminobenzoate, isobutyl 2-aminobenzoate, methyl 4-chloro-2-amino-benzoate, methyl 5-chloro-2-aminobenzoate, methyl 6-chloro-2-aminobenzoate, methyl 3,5-dichloro-2-aminobenzoate, methyl 4,6-dichloro-2-aminobenzoate, methyl 5-bromo-2-aminobenzoate, methyl 4-nitro-2-aminobenzoate, methyl 5-nitro-2-aminobenzoate, methyl 4-methyl-2-aminobenzoate, methyl 5-methyl-2-aminobenzoate, methyl 6-methyl-2-aminobenzoate, methyl 4-trifluoromethyl-2-aminobenzoate, methyl 4-methoxy-2-aminobenzoate, phenyl 4-methoxy-3-aminobenzoate, methyl 4-carbamoyl-2-aminobenzoate, methyl 4-acetylamino-2-aminobenzoate, methyl 4-benzoylamino-2-aminobenzoate, methyl 4-(2,5-dichlorobenzoylamino)-2-aminobenzoate, methyl 4-sulphamoyl-2-aminobenzoate, methyl 2-aminonaphthalene-3-carboxylate, methyl 4-methyl-3-aminobenzoate, dimethyl 1-aminobenzene-2,5-dicarboxylate, dimethyl 1-aminobenzene-3,5-dicarboxylate, 2-aminobenzoic acid amide, 4-aminobenzoic acid amide, 4-chloro-3-aminobenzoic acid amide, 4,6-dichloro-3-aminobenzoic acid amide, 3-amino-4-methoxy-benzoic acid amide, 3-amino-4-methoxy-benzoic acid phenylamide, 3-amino-4-methylbenzoic acid methylamide, 3-amino-4-methylbenzoic acid (2,4-dimethylphenyl)-amide, 1-aminobenzene-3,5-dicarboxylic acid diamide, 3-amino-4-methylbenzoic acid (2,5-dichlorophenyl)-amide, 3-amino-4-methoxycarbonylbenzoic acid amide, 3-amino-4-methoxycarbonylbenzoic acid phenylamide, 3-amino-4-methoxycarbonylbenzoic acid (2,5-dichlorophenyl)-amide, 3-amino-4-methoxybenzenesulphonic acid methylamide, 3-amino-4-methoxybenzenesulphonic acid diethylamide, 2,5-dimethoxy-4-aminobenzenesulphonic acid methylamide, 2-methyl-5-methoxy-4-aminobenzenesulphonic acid methylamide, 3-amino-4-methylbenzenesulphonic acid phenylamide, 4-amino-2,5-dimethoxybenzenesulphonic acid methylamide, 4-amino-2-methyl-5-methoxybenzenesulphonic acid methylamide, 2-chloro-1-aminonaphthalene, 1-amino-2-methoxynaphthalene, 1-amino-4-nitronaphthalene, 2-amino-5-nitronaphthalene, 2-aminothiazole, 2-amino-4-methylthiazole, 2-amino-5-chlorothiazole, 2-amino-5-nitrothiazole, methyl 2-amino-4-methylthiazole-5-carboxylate, 2-amino-4-methylthiazole-5-carboxylic acid dimethylamide, 2-aminobenzthiazole, 2-amino-6-methylbenzthiazole, 2-amino-5-methoxybenzthiazole, 2-amino-6-methoxybenzthiazole, 2-amino-6-chlorobenzthiazole, 2-amino-6-methylsulphonylbenzthiazole, 6-methyl-2-(4-aminophenyl)-benzthiazole, 5-amino-3-phenyl-1,2,4-thiadiazole, 2-amino-4-methylcarbostyril, 6-amino-4-methyl-2-chlorocarbostyril, 3-amino-4-methoxybenzoxazole, 6-amino-2,4-dihydroxyquinazoline.

1-Aminoanthraquinone, 2-aminoanthraquinone, 1-amino-2-chloroanthraquinone, 1-amino-4-chloroanthraquinone, 1-amino-5-chloroanthraquinone, 1-amino-6-chloroanthraquinone, 1-amino-6(7)-chloroanthraquinone (mixture), 1-amino-5,8-dichloroanthraquinone, 1-amino-2-bromoanthraquinone, 1-amino-2,4-dibromoanthraquinone, 1-amino-6,7-dichloroanthraquinone, 1-amino-6-fluoroanthraquinone, 1-amino-7-fluoroanthraquinone, 1-amino-6,7-difluoroanthraquinone, 2-amino-1-chloroanthraquinone, 2-amino-3-chloroanthraquinone, 2-amino-3-bromoanthraquinone, 1-amino-4-nitroanthraquinone, 1-amino-5-nitroanthraquinone, 1-amino-2-methylanthraquinone, 1-amino-2-methyl-4-chloroanthraquinone, 1-amino-2-methyl-4-bromoanthraquinone, 1-aminoanthraquinone-2-carboxylic acid, 1-aminoanthraquinone-2-carboxylic acid amide, methyl 1-aminoanthraquinone-2-carboxylate, 1-amino-4-nitroanthraquinone-2-carboxylic acid, 1-amino-2-acetylanthraquinone, 1-amino-5-benzoylaminoanthraquinone, 1-amino-4-benzoylaminoanthraquinone, 1-amino-4-hydroxyanthraquinone, 1-amino-5-hydroxyanthraquinone, 1-amino-4-methoxyanthraquinone, 1-amino-2-methoxy-4-hydroxyanthraquinone, 1-amino-4-methylaminoanthraquinone, 1-amino-4-cyclohexylaminoanthraquinone, 1-amino-4-anilinoanthraquinone, 1-amino-6-methylmercaptoanthraquinone, 2-phenyl-6-amino-4,5-phthaloylbenzimidazole, 6-chloro-2-amino-3,4-phthaloylacridone, 7-chloro-2-amino-3,4-phthaloylacridone, 5-chloro-8-amino-3,4-phthaloylacridone, 4-aminoanthrapyridone, 5-aminoanthrapyridone, 1,5-diaminoanthraquinone, 1,4-diaminoanthraquinone, 1,8-diaminoanthraquinone, 2,6-diaminoanthraquinone, 1,5-diamino-4-chloroanthraquinone, 1,4-diamino-5-nitroanthraquinone, 1,5-diamino-2,4,6,8-tetrabromoanthraquinone, 1,5-diamino-4,8-dihydroxyanthraquinone, 1,8-diamino-4,5-dihydroxyanthraquinone, 4,4'-diamino-1,1'-dianthrimide, 4,4'-diaminobiphenyl, 4,4'-diamino-3,3'-dimethoxybiphenyl, 4,4'-diamino-3,3'-diethoxybiphenyl, 4,4'-diamino-2,2'-dichlorobiphenyl, 4,4'-diamino-3,3'-dichloro-biphenyl, 4,4'-diamino-2,2', 5,5'-tetrachlorobiphenyl, 4,4'-diamino-2-nitrobiphenyl, 4,4'-diamino-3-methylbiphenyl, 4,4'-diamino-2,2'-dimethylbiphenyl, 4,4'-diamino-3,3'-dimethylbiphenyl, 4,4'-diamino-3,3'-dimethoxy-6,6'-dichlorobiphenyl, 1-amino-8-benzoylaminoanthraquinone and 1-amino-2-bromo-4-(4-methylphenylsulphonylamino)-anthraquinone.

Preferred diazo components are those of the benzene and anthraquinone series.

Particularly preferred dyestuffs are those of the formula $$\text{(VI)}$$

wherein $R_3$ denotes hydrogen or methyl, $R_4$ denotes hydrogen, $C_1$-$C_4$-alkyl, $C_1$-$C_4$-alkoxy, fluorine, chlorine, bromine, nitro, $C_1$-$C_4$-alkylcarbonylamno or $C_1$-$C_4$-alkylsulphonylamino, $R_5$ denotes hydrogen, halogen, such as fluorine, chlorine and bromine, $C_1$-$C_4$-alkyl, $C_1$-$C_4$-alkoxy, nitro, cyano, $C_1$-$C_4$-alkylsulphonyl, trifluoromethyl, $C_1$-$C_4$-alkylcarbonylamino, benzoylamino which is optionally substituted by $C_1$-$C_4$-alkyl, $C_1$-$C_4$-alkoxy, fluorine, chlorine, bromine or nitro, $C_1$-$C_4$-alkoxycarbonyl, or carboxamide or sulphonamide which are optionally monosubstituted or disubstituted by $C_1$-$C_4$-alkyl, phenyl or benzyl, it being possible for phenyl and benzyl to be further substituted by $C_1$-$C_4$-alkyl, $C_1$-$C_4$-alkoxy, fluorine, chlorine, bromine and nitro, $R_6$ denotes hydrogen, halogen, such as fluorine, chlorine and bromine, $C_1$-$C_4$-alkyl, cyano, $C_1$-$C_4$-alkoxy, nitro or trifluoromethyl and $R_7$ denotes hydrogen, chlorine, $C_1$-$C_4$-alkyl or $C_1$-$C_4$-alkoxy.

Further preferred dyestuffs correspond to the formula $$\text{(VII)}$$

wherein $R_3$ and $R_4$ have the abovementioned meaning, $R_8$ denotes hydrogen, halogen, such as fluorine, chlorine and bromine, nitro, $C_1$-$C_4$-alkyl, $C_1$-$C_4$-alkoxy, $C_1$-$C_4$-alkylamino, benzylamino, cyclohexylamino, $C_1$-$C_4$-alkylmercapto, phenylmercapto which is optionally substituted by $C_1$-$C_4$-alkyl, $C_1$-$C_4$-alkoxy, fluorine, chlorine, bromine or nitro, $C_1$-$C_4$-alkylcarbonyl, $C_1$-$C_4$-alkoxycarbonyl, phenylamino which is optionally substituted by $C_1$-$C_4$-alkyl, $C_1$-$C_4$-alkoxy, chlorine or nitro, carboxamide which is optionally monosubstituted or disubstituted by $C_1$-$C_4$-alkyl, benzyl or phenyl, it being possible for phenyl to be substituted by $C_1$-$C_4$-alkyl, $C_1$-$C_4$-alkoxy, fluorine, chlorine, bromine or nitro, or carboxyl, hydroxyl, $C_1$-$C_4$-alkylcarbonylamino or benzoylamino which is optionally substituted by $C_1$-$C_4$-alkyl $C_1$-$C_4$-alkoxy, chlorine, bromine or nitro, $C_1$-$C_4$-alkylsulphonylamino or phenylsulphonylamino which is optionally substituted by $C_1$-$C_4$-alkyl, $C_1$-$C_4$-alkoxy, fluorine, chlorine, bromine or nitro, $R_9$ denotes hydrogen, chlorine or hydroxyl, $R_{10}$ denotes hydrogen, halogen, such as fluorine, chlorine or bromine, nitro, $C_1$-$C_4$-alkyl, $C_1$-$C_4$-alkoxy, $C_1$-$C_4$-alkylamino, $C_1$-$C_4$-alkylmercapto, phenylmercapto which is optionally substituted by $C_1$-$C_4$-alkyl, $C_1$-$C_4$-alkoxy, fluorine, chlorine, bromine or nitro, $C_1$-$C_4$-alkoxycarbonyl, $C_1$-$C_4$-alkylcarbonyl, benzylamino, cyclohexylamino, phenylamino which is optionally substituted by $C_1$-$C_4$-alkyl, $C_1$-$C_4$-alkoxy, chlorine, bromine or nitro, carboxyl, hydroxyl, carboxamide which is optionally monosubstituted or disubstituted by $C_1$-$C_4$-alkyl, benzyl or phenyl, it being possible for phenyl to be substituted by $C_1$-$C_4$-alkyl, $C_1$-$C_4$-alkoxy, fluorine chlorine, bromine or nitro, or $C_1$-$C_4$-alkyl, carbonylamino, benzoylamino which is optionally substituted by $C_1$-$C_4$-alkyl, $C_1$-$C_4$-alkoxy, chlorine, bromine or nitro, $C_1$-$C_4$-alkylsulphonylamino or phenylsulphonylamino which is optionally substituted by $C_1$-$C_4$-alkyl, $C_1$-$C_4$-alkoxy, fluorine, chlorine, bromine or nitro and $R_{11}$ denotes hydrogen, halogen, such as fluorine, chlorine and bromine, or hydroxyl.

Pigments of the formula $$\text{(VIII)}$$

wherein $R_{12}$, $R_{13}$, $R_{14}$ and $R_{15}$ denote hydrogen, chlorine, bromine, carboxyl, $C_1$-$C_4$-alkoxycarbonyl, carboxamide, $C_1$-$C_4$-alkylcarbonylamino, benzoylamino which is optionally substituted by 1 or 2 nitro or 1 to 5 chlorine or bromine, or $C_1$-$C_4$-alkylsulphonylamino or phenylsulphonylamino which is optionally substituted by methyl, methoxy or chlorine, are very particularly preferred.

The azo pigments V are prepared by coupling diazotised aromatic amines of the formula $$D-NH_2 \quad \text{(IX)}$$

wherein

D has the abovementioned meaning, with the heterocyclic compounds I.

Several processes can be used for the coupling reactions:

(1) The aqueous or alkaline aqueous suspension or solution of the coupling component is added to the acid, aqueous diazonium salt solution. The mixture is stirred until the reaction has ended and the dyestuff is purified by heating in an organic solvent such as n-butanol, toluene, chlorobenzene, pyridine, nitrobenzene, o-dichlorobenzene, 1,2,4-trichlorobenzene, tetramethylenesulphone, dimethylformamide, N-methylpyrrolidone, ethylene glycol dimethyl ether or ethylene glycol diethyl ether.

(2) The diazo component VIII is diazotised in an organic solvent, such as dimethylformamide, dimethylacetamide, dimethylsulphoxide, tetramethylenesulphone, tetraphenylurea, N-methylpyrrolidone, nitrobenzene, o-dichlorobenzene, 1,2,4-trichlorobenzene, ethylene glycol dimethyl ether, ethylene glycol diethyl ether or acetic acid, in the presence of an acid, such as sulphuric acid, phosphoric acid, benzenesulphonic acid, ethanesulphonic acid, p-toluenesulphonic acid, naphthalene-2,6-disulphonic acid, formic acid, acetic acid, dichloroacetic acid, 2,4-dichlorobenzoic acid, oxalic acid, succinic acid, maleic acid, tartaric acid or terephthalic acid, with organic nitrites, such as methyl nitrite, ethyl nitrite or iso-amyl nitrite, or advantageously with nitrites of glycols and glycol derivatives, such as methoxyethyl nitrite or ethoxyethyl nitrite, or alkali metal nitrites, such as sodium nitrite. A suspension of the coupling component, appropriately in the same solvent, is then stirred in. After the coupling reaction has ended, the crude product is purified in the coupling solution by raising the temperature to 90° to 200° C. and is isolated by filtering off.

The second process can also be varied in such a way that the diazo component and coupling component are initially introduced in the organic solvent and the alkyl nitrite or alkali methane nitrite is added, so that diazotisation and coupling take place at the same time. This process variant also is appropriately followed by a high temperature treatment to purify the pigment prepared in this way.

(3) The coupling component I is converted, in an organic solvent such as dimethylformamide, dimethylacetamide, dimethylsulphoxide, tetramethylenesulphone, tetraphenylurea, N-methylpyrrolidone, nitrobenzene, nitrotoluene, o-dichlorobenzene, 1,2,4-trichlorobenzene, ethylene glycol dimethyl ether or ethylene glycol diethyl ether, at temperatures between 20° and 180° C. to its salt with organic acids, such as formic acid, acetic acid, chloroacetic acid, dichloroacetic acid, dichlorobenzoic acid, oxalic acid or maleic acid. The diazo component is then added and the diazotisation and coupling reactions are carried out at temperatures of −10° to 100° C. by adding alkali metal nitrites, which can be employed in the crystalline form or as aqueous solutions, or organic nitrites, such as amyl nitrite, methyl nitrite or the nitrites of glycols. In this case also, the process is appropriately followed by a high temperature treatment of the pigment prepared in this way.

The pigments of the formula V are obtained in a form suitable for pigments or can be converted to the suitable form by after-treatment processes which are in themselves known, for example by dissolving or swelling in strong inorganic acids, such as sulphuric acid, and discharging onto ice. The state of fine division can also be achieved by grinding with or without grinding assistants, such as inorganic salts or sand, optionally in the presence of solvents such as toluene, xylene, dichlorobenzene or N-methylpyrrolidone. The tinctorial strength and transparency of the pigment can be influenced by varying the after-treatment.

Because of their fastness to light and fastness to migration, the pigments of the formula V are suitable for very diverse pigment applications. The pigments according to the invention can be used to prepare very fast pigmented systems, such as mixtures with other substances, formulations, paints, printing pastes, coloured paper and coloured macromolecular materials. Mixtures with other substances can be understood as meaning, for example, those with inorganic white pigments, such as titanium dioxide (rutile), or with cement. Formulations are, for example, flush pastes with organic liquids or pastes and refined pastes with water, dispersing agents and optionally preservatives. The term paint represents, for example, lacquers which dry by physical means or by oxidation, stoving lacquers, reactive lacquers, two-component lacquers, emulsion paints for weather-resistant coatings and distempers. Printing pastes are to be understood as meaning those for paper, textile and tinplate printing. The macromolecular materials can be of natural origin, such as rubber, obtained by chemical modification, such as acetylcellulose, cellulose butyrate or viscose, or synthetically produced, such as polymers, polyaddition products and polycondensation products. Plastic materials such as polyvinyl chloride, polyvinyl acetate, polyvinyl propionate, polyolefines, for example polyethylene or polypropylene, polyesters, for example polyethylene terephthalate, polyamides, high molecular weight polyamides, polymers and copolymers of acrylates, methacrylates, acrylonitrile, acrylamide, butadiene and styrene and also polyurethanes and polycarbonates may be mentioned. The substances pigmented with the products claimed can be in any desired form. The pigments of the formula V are also particularly suitable for spin-dyeing polyacrylonitrile.

The pigments V according to the invention are, furthermore, outstandingly fast to water, fast to oil, fast to acid, fast to lime, fast to alkali, fast to solvents, fast to cross-dyeing, fast to over-spraying, fast to sublimation, heat-resistant and stable to vulcanising, have a high tinctorial strength and can be dispersed well in plastic materials.

EXAMPLE 1

300 ml of diethyl malonate, 580 g of anthranilamide and 6 g of diazabicyclooctane are added to 1.2 l of o-dichlorobenzene. A water separator is then placed on the reaction vessel and the mixture is stirred for 5 hours at 175° C. It is then allowed to cool to 80° C. whilst stirring, and the precipitate is filtered off and rinsed with o-dichlorobenzene. After drying, 480 g (84% of theory) of the compound of the formula

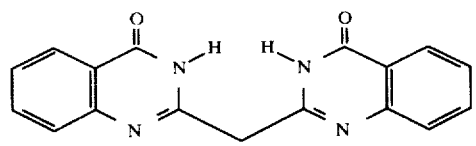

are obtained in the form of a yellowish powder with a melting point above 330° C. The composition is confirmed, inter alia, by elementary analysis.

Found (calculated): C 67.4 (67.0), H 4.3 (4.0), N 18.3 (18.4)

The following compounds are prepared by the process given in Example 1 using substituted anthranilamides in place of anthranilamide and are purified by recrystallisation from dimethylformamide.

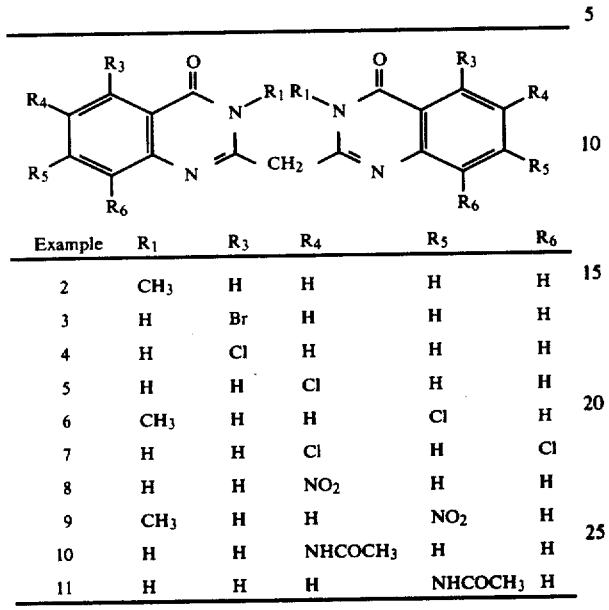

| Example | R$_1$ | R$_3$ | R$_4$ | R$_5$ | R$_6$ |
|---|---|---|---|---|---|
| 2 | CH$_3$ | H | H | H | H |
| 3 | H | Br | H | H | H |
| 4 | H | Cl | H | H | H |
| 5 | H | H | Cl | H | H |
| 6 | CH$_3$ | H | H | Cl | H |
| 7 | H | H | Cl | H | Cl |
| 8 | H | H | NO$_2$ | H | H |
| 9 | CH$_3$ | H | H | NO$_2$ | H |
| 10 | H | H | NHCOCH$_3$ | H | H |
| 11 | H | H | H | NHCOCH$_3$ | H |

The analytical values found for the individual products agree well with the calculated values and are not given separately here. All of the compounds are yellow powders which have not yet melted at 300° C. and which do not dissolve or dissolve only slightly in the conventional organic solvents.

EXAMPLE 12

(a) 35 g of 1-amino-5-benzoylaminoanthraquinone (87% pure) are dissolved in 180 g of sulphuric acid, with ice-cooling, and diazotised with 30 g of nitrosylsulphuric acid (42% strength in sulphuric acid). After diluting with 250 g of water, the excess nitrite is destroyed with amidosulphonic acid and a suspension of 30 g of the compound obtained according to Examples 1 in 150 g of 20% strength aqueous potassium hydroxide solution is added in portions at 70° C. After 30 minutes, the mixture is filtered hot and the material on the filter is washed with hot water until neutral. The product is filtered off and, in 300 ml of nitrobenzene, is freed from water by distillation at 130° C.

The product is then heated briefly to 160° C. in nitrobenzene in order to obtain a better pigment quality. The mixture is allowed to cool to 100° C. and the product is filtered off, washed with nitrobenzene and methanol and dried at 80° in vacuo. 52 g (90% of theory) of the orange coloured pigment of the formula

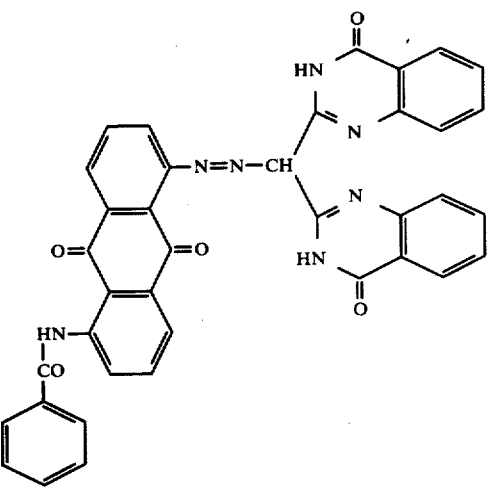

are thus obtained.

(b) 7 g of 1-amino-5-benzoylaminoanthraquinone (87% pure), 7.5 g of the compound obtained according to Example 1 and 5 g of dichloroacetic acid are added to 80 g of nitrobenzene. 3 g of isoamyl nitrite in 17 g of nitrobenzene are added dropwise at 70° C. The mixture is stirred for 3 hours at 70° C. and is then heated briefly to 160° C. and the precipitate is filtered off and rinsed with hot nitrobenzene and methanol. After drying, 11 g (94% of theory) of the pigment mentioned in Example 12a are obtained.

(c) 7 g of 1-amino-5-benzoylamino-anthraquinone (87% pure) are diazotised in 90 g of dimethylformamide with 14 g of nitrosylsulphuric acid. After destroying the excess nitrite with amidosulphonic acid, 7.5 g of the product obtained according to Example 1 are added and the mixture is stirred for 2 hours at 70° C. It is then heated briefly to 140° C. and the precipitate is filtered off at 80° C., rinsed with dimethylformamide and hot water and dried. 9 g (77% of theory) of the pigment mentioned in Example 12a are obtained.

(d) 600 g of the compound obtained according to Example 1 are stirred in a mixture of 4.5 l of nitrobenzene and 1 l of formic acid (85%) for 3 hours at 40° C. During this time the coupling component crystallises as the monoformate. 700 g of 1-amino-5-benzoylaminoanthraquinone (87% pure) are then added and a solution of 350 g of NaNO$_2$ in 500 ml of water is added dropwise. The mixture is stirred for a further 3 hours at 40° C., heated to remove water in vacuo and subjected to a heat treatment at 150° C. for 1 hour. The product is filtered off at 100° C., washed with nitrobenzene, methanol and water and dried. 1.08 kg (92% of theory) of the pigment mentioned in Example 12a are obtained.

EXAMPLE 13

4.1 g of 2-nitroaniline in 90 g of dimethylformamide are diazotised at 5° C. with 9 g of nitrosylsulphuric acid (42% strength in sulphuric acid). A suspension of the product obtained according to Example 1 in 20 g of dimethylformamide is then added and after stirring for 2 hours at 5° C. the mixture is filtered. After washing with dimethylformamide and hot water, the product is dried. 13 g (96% of theory) of the yellow pigment of the formula

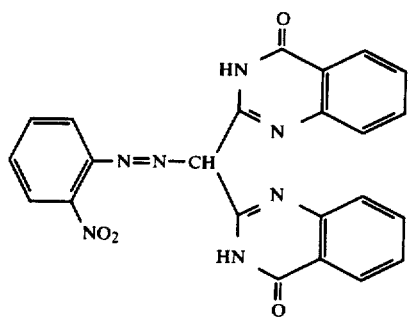

are obtained.

Using the diazo components listed in the table which follows, in place of 2-nitroaniline, corresponding azo pigments of the indicated colour shades are obtained by the process described in Example 13.

TABLE 1

| Examples | Diazo component | Colour shade |
|---|---|---|
| 14 | aniline | greenish-tinged yellow |
| 15 | 2,4-dimethylaniline | greenish-tinged yellow |
| 16 | 2-chloroaniline | yellow |
| 17 | 3-amino-4-chlorobenzamide | yellow |
| 18 | 3-nitroaniline | greenish-tinged yellow |
| 19 | 2-nitro-4-chloroaniline | yellow |
| 20 | 2-chloro-4-nitroaniline | yellow |
| 21 | anthranilamide | yellow |
| 22 | 3-trifluoromethylaniline | greenish-tinged yellow |
| 23 | 2-trifluoromethyl-4-chloroaniline | greenish-tinged yellow |
| 24 | 2-methoxyaniline | yellow |
| 25 | 4-methoxyaniline | yellow |
| 26 | methyl 4-aminobenzoate | yellow |
| 27 | dimethyl 5-amino-iso-phthalate | greenish-tinged yellow |
| 28 | 3,4-dicyanoaniline | yellow |
| 29 | 4-methoxy-4'-amino-diphenylamine | reddish-tinged yellow |
| 30 | 4-aminoazobenzene | reddish-tinged yellow |
| 31 | 3,3'-dichloro-4,4'-diaminobiphenyl | yellow |
| 32 | 3,3'-dimethoxy-4,4'-diaminobiphenyl | red |
| 33 | 4-(4-aminobenzoylamino)-aniline | yellow |
| 34 | 1-aminoanthraquinone | orange |
| 35 | 2-aminoanthraquinone | reddish-tinged yellow |
| 36 | 4-chloro-1-amino-anthraquinone | orange |
| 37 | 2-methyl-1-amino-anthraquinone | orange |
| 38 | 4-methoxy-1-amino-anthraquinone | red |
| 39 | 2-carboxy-1-amino-anthraquinone | orange |
| 40 | 2-aminothiazole | orange |
| 41 | 2-aminobenzthiazole | orange |

Further pigments with the colour shades indicated in the table which follows are obtained by the process described in Example 13 when the diazo components listed in the second column are used in place of 2-nitroaniline and the coupling components listed in the third column are used in place of the coupling component obtained according to Example 1.

TABLE 2

| Example | Diazo component | Coupling component | Colour shade |
|---|---|---|---|
| 42 | anthranilamide | Example 2 | yellow |
| 43 | 4-nitro-2-chloroaniline | Example 2 | yellow |
| 44 | 3-nitroaniline | Example 5 | greenish-tinged yellow |
| 45 | 1-aminoanthraquinone | Example 6 | orange |
| 46 | 1-amino-5-nitro-anthraquinone | Example 2 | orange |
| 47 | 1-amino-4-chloro-anthraquinone | Example 10 | orange |
| 48 | 1-amino-5-benzoylamino-anthraquinone | Example 8 | orange |
| 49 | 1-amino-4-methoxy-anthraquinone | Example 8 | red |
| 50 | 2-aminobenzthiazole | Example 2 | orange |

EXAMPLE 51

(a) 8 g of the finely divided pigment obtained according to Example 12 are ground with a stoving lacquer consisting of 25 g of coconut oil alkyd resin (40% of coconut oil), 10 g of melamine resin, 50 g of toluene and 7 g of glycol monomethyl ether on an automatic Hoover-Muller grinding machine. The mixture is applied to the substrate to be lacquer-coated and the lacquer is cured by stoving at 130° C. and orange lacquer coatings with very good fastness to over-lacquering and outstanding fastness to light and weathering are obtained.

Pigmented stoving lacquers with the same fastness properties are obtained when 15–25 g of the indicated alkyd resin or of an alkyd resin based on cottonseed oil, dehydrated castor oil, castor oil or synthetic fatty acids are used and, in place of the indicated amount of melamine resin, 10–15 g of the melamine resin mentioned or of a condensation product of formaldehyde with urea or with benzoguanamine are employed.

(b) If, in place of the indicated amount of pigment, 1 to 10 g of a mixture of titanium dioxide (rutile type) with the pigment indicated in Example 51a in a ratio of 0.5–50:1 are ground into the lacquer indicated in Example 51a, identical further processing gives lacquer coatings which have the same fastness properties and an orange colour shade shifted towards white with increasing titanium dioxide content.

EXAMPLE 52

6 g of the finely divided pigment according to Example 12 are ground into 100 g of a nitrocellulose lacquer which consists of 44 g of collodion cotton (low viscosity, 35% strength, butanol-moist), 5 g of dibutyl phthalate, 40 g of ethyl acetate, 20 g of toluene, 4 g of n-butanol and 10 g of glycol monomethyl ether. After spreading and drying, orange-coloured lacquer coatings with outstanding fastness to light and fastness to over-lacquering are obtained. The same results are obtained which nitrolacquers are used which contain 10–15 g of nitrocellulose, 5–10 g of plasticizer and 70–85 g of a solvent mixture in which aliphatic esters, such as ethyl acetate and butyl acetate, and aromatic compounds, such as toluene and xylene, and smaller proportions of aliphatic ethers, such as glycol ether, and alcohols, such as butanol, are preferably used. Plasticisers can be understood as meaning, for example: phthalic acid esters, such as dioctyl phthalate and dibutyl phthalate, esters of phosphoric acids and castor oil, on its own or in combination with oil-modified alkyd resins.

Lacquer coatings with similar fastness properties are obtained when other spirit lacquers, celluloid lacquers and nitrolacquers which dry by physical means, air-drying oil lacquers, synthetic resin lacquers and nitro combination lacquers and oven-drying and air-drying epoxide resin lacquers, optionally in combination with urea resins, melamine resins, alkyd resins or phenol resins, are used.

EXAMPLE 53

5 g of the pigment according to Example 12, which has been brought into a state of fine division, are ground in 100 g of a paraffin-free drying unsaturated polyester resin in a porcelain ball mill. 10 g of styrene, 59% of melamine/formaldehyde resin and 1 g of a paste of 40 g of cyclohexanone peroxide and 60% of dibutyl phthalate are stirred well with the ground mixture and finally 4 g of drier solution (10% strength cobalt naphthenate in white spirit) and 1 g of silicone oil solution (1% strength in xylene) are admixed. The mixture is applied to primed wood and an orange-coloured lacquer coating which has a high gloss and is resistant to water and fast to weathering and has outstanding fastness to light is obtained.

If amine-curing epoxide resin lacquers containing dipropylenediamine as the amino component are used in place of the reactive lacquer based on unsaturated polyester resins, orange-coloured lacquer coatings with outstanding fastness to weathering and fastness to efflorescence are obtained.

EXAMPLE 54

100 g of a 65% strength solution of an aliphatic polyester containing about 8% of free hydroxyl groups in glycol monoethyl ether-acetate are ground with 5 g of the pigment obtained according to Example 12 and then mixed well with 44 g of a 67% strength solution of the reaction product of 1 mol of trimethylolpropane with 3 mol of toluylene diisocyanate. Without the pot life being impaired, orange-coloured polyurethane lacquer coatings which have a high gloss and outstanding fastness to efflorescence, fastness to light and fastness to weathering are obtained after applying the mixture and reaction of the components.

Pigmentations with similar fastness properties are obtained by the use of other two-component lacquers based on aromatic or aliphatic isocyanates and hydroxyl group-containing polyethers or polyesters, and also with moisture-drying polyisocyanate lacquers which give polyurea lacquer coatings.

EXAMPLE 55

5 g of a refined paste obtained by kneading 50 g of the pigment obtained according to Example 12 with 15 g of an arylpolyglycol ether emulsifier and 35 g of water are mixed with 10 g of barytes, as the filler, 10 g of titanium dioxide (rutile type), as the white pigment, and 40 g of an aqueous emulsion paint containing about 50% of polyvinyl acetate. The paste is spread and, after drying, orange-coloured coatings with very good fastness to lime and cement and also outstanding fastness to weathering and light are obtained.

The refined paste obtained by kneading is likewise suitable for pigmenting clear polyvinyl acetate emulsion paints, for emulsion paints which contain copolymers of styrene and maleic acids as the binders and also emulsion paints based on polyvinyl propionate, polymethacrylate or polybutadiene/styrene.

EXAMPLE 56

10 g of the pigment paste mentioned in Example 55 are mixed with a mixture of 5 g of chalk and 5 g of 20% strength size solution. This gives an orange-coloured wallpaper paint with which coatings of outstanding fastness to light are obtained. Other nonionic emulsifiers, such as the reaction products of nonylphenyol with ethylene oxide, or ionic wetting agents, such as the sodium salts of alkylarylsulphonic acids, for example of dinaphthylmethanedisulphonic acid, sodium salts of substituted sulpho fatty acid esters and sodium salts of paraffin sulphonic acids in combination with alkylpolyglycol ethers can also be used to prepare the pigment paste.

EXAMPLE 57

A mixture of 65 g of polyvinyl chloride, 35 g of diisooctyl phthalate, 2 g of dibutyl-tin mercaptide, 0.5 g of titanium dioxide and 0.5 g of the pigment of Example 12 is coloured in a mixing mill at 165° C. An intensely orange-coloured mass is obtained which can be used to prepare films or shaped articles. The coloration is distinguished by outstanding fastness to light and very good fastness to plasticisers.

EXAMPLE 58

0.2 g of the pigment according to Example 12 are mixed with 100 g of polyethylene, polypropylene or polystyrene granules. The mixture can either be injection moulded direct at 220° to 280° C. in an injection moulding machine or can be processed in an extruder to give coloured bars or processed in a mixing mill to give coloured hides. The bars or hides are optionally granulated and injection mouled in an injection moulding machine.

The orange-coloured mouldings have very good fastness to light and migration. Synthetic polyamides of caprolactam or adipic acid and hexamethylenediamine or the condensation products of terephthalic acid and ethylene glycol can be coloured in a similar way at 280°-300° C., if appropriate under a nitrogen atmosphere.

EXAMPLE 59

1 g of the pigment according to Example 12, 10 g of titanium dioxide (rutile type) and 100 g of a copolymer based on acrylonitrile/butadiene/styrene and in the powder form are mixed and coloured on a roll mill at 140°-180° C. An orange-coloured hide is obtained and this is granulated and the granules are injection moulded in an injection moulding machine at 200°-250° C. Orange-coloured mouldings with very good fastness to light and migration and excellent stability to heat are obtained.

Plastics based on cellulose acetate, cellulose butyrate and mixtures thereof are coloured, with similar fastness properties, in a similar manner, but at temperatures of 180°-220° C. and without the addition of titanium dioxide.

EXAMPLE 60

0.2 g of the pigment according to Example 12 is mixed, in the finely divided form, with 100 g of a plastic based on polycarbonate, in an extruder or a screw kneader at 250° to 280° C. and the mixture is processed to granules. Orange-coloured, transparent granules with outstanding fastness to light and stability to heat are obtained.

EXAMPLE 61

90 g of a slightly branched polypropylene glycol with a molecular weight of 2,500 and a hydroxyl number of 56, 0.25 g of endoethylenepiperazine, 0.3 g of tin-II octoate, 1.0 g of a polyether siloxane, 3.5 g of water and 12.0 g of a ground mixture of 10 g of the pigment according to Example 12 in 50 g of the indicated polypropylene glycol are mixed together well and the mixture is then intimately mixed with 45 g of toluylene diisocyanate (80% of the 2,4 and 20% of the 2,6 isomer) and the resulting mixture is poured into a mould. The mixture becomes turbid after about 6 seconds and foam formation takes place. After 70 seconds, an intensely orange-coloured, soft polyurethane foam has formed, the pigmentation of which has outstanding fastness to light.

EXAMPLE 62

90 g of a slightly branched polyester of adipic acid, diethylene glycol and trimethylolpropane, with a molecular weight of 2,000 and a hydroxyl number of 60, are mixed with the following components: 1.2 g of dimethylbenzylamine, 2.5 g of sodium castor oil sulphate, 2.0 g of an oxethylated, benzylated oxydiphenyl, 1.75 g of water and 12 g of a paste prepared by grinding 10 g of the pigment according to Example 12 in 50 g of the abovementioned polyester. After mixing, 40 g of toluylene diisocyanate (65% of the 2,4 isomer and 35% of the 2,6 isomer) are stirred in, whilst stirring, and the mixture is poured into a mould and foamed. After 60 seconds an orange-coloured, soft polyurethane foam has formed, the coloration of which is distinguished by very good fastness to light.

EXAMPLE 63

Using a print paste prepared by grinding 35 g of the pigment according to Example 12 and 65 g of linseed oil and adding 1 g of Sicoativ (Co naphthenate, 50% strength in white spirit), orange-coloured offset prints of high billiance and depth of colour and very good fastness to light and lacquering are obtained. The use of this print paste in letterpress printing, collotype printing, lithography or die stamping results in orange-coloured prints with similar fastness properties. If the pigment is used for colouring tin printing inks or gravure inks of low viscosity or printing inks, orange-coloured prints with similar fastness properties are obtained.

EXAMPLE 64

A print paste is prepared from 10 g of the pigment refined paste indicated in Example 55, 100 g of 3% strength tragacanth, 100 g of an aqueous 50% strength egg albumin solution and 25 g of a nonionic wetting agent. A textile fibre fabric is printed and steamed at 100° C. and an orange-coloured print is obtained which is distinguished by outstanding fastness properties, especially fastness to light. Further binders which can be used for fixing on the fibre, for example those based on synthetic resins, British gum or cellulose glycolate, can be used in the print recipe in place of the tragacanth and egg albumin.

EXAMPLE 65

A mixture of 100 g of light crepe, 2.6 g of sulphur, 1 g of stearic acid, 1 g of mercaptobenzthiazole, 0.2 g of hexamethylenetetramine, 5 g of zinc oxide, 60 g of chalk and 2 g of titanium dioxide (anatase type) is coloured in a mixing mill at 50° C. with 2 g of the pigment obtained according to Example 12 and the mixture is then vulcanised for 12 minutes at 140° C. An orange-coloured vulcanisate with very good fastness to light is obtained.

EXAMPLE 66

100 g of a 20% strength aqueous paste of the pigment according to Example 12, for example prepared by dissolving the dyestuff in 96% strength sulphuric acid, discharging onto ice, filtering and washing the product until neutral with water, are added to 22.5 l of an aqueous, approximately 9% strength viscose solution in a stirring apparatus. The coloured mass is stirred for 15 minutes, the air is then removed and the mass is subjected to a spinning and desulphurising process.

Orange-coloured filaments or films with very good fastness to light are obtained.

EXAMPLE 67

10 kg parts of a paper pulp containing 4 g of cellulose per 100 g are treated in a hollander for about 2 hours. During this time 4 g of resin size, then 30 g of an approximately 15% strength pigment dispersion, obtained by grinding 4.8 g of the pigment obtained according to Example 12 with 4.8 g of dinaphthylmethanedisulphonic acid and 22 g of water in a ball mill, and then 5 g of aluminium sulphate are added at quarter hour intervals.

After finishing on the papermaking machine, an orange-coloured paper with outstanding fastness to light is obtained.

EXAMPLE 68

The orange pigmented paper prepared according to Example 67 is saturated with a 55% strength solution of a urea/formaldehyde resin in n-butanol and baked at 140° C. An orange-coloured laminate paper with very good fastness to migration and outstanding fastness to light is obtained.

A laminate paper with the same fastness properties is obtained by laminating a paper which has been printed by the gravure printing process with a print paste which contains the orange-coloured refined pigment paste indicated in Example 55 and water-soluble or saponifiable binders.

EXAMPLE 69

20 parts of the pigment obtained according to Example 12 e are pre-dispersed in 50 parts of dimethylformamide using a dissolver and, optionally with the addition of a dispersing agent and of 50 parts of a 10% strength polyacrylonitrile solution in dimethylformamide, subjected to grinding in a bead mill. After separating off residual coarse particles by known processes, the pigment mass is added in portions to a spinning solution of polyacrylonitrile and the solution is homogenised and spun to filaments by a dry or wet spinning process which is known and customary industrially.

The colorations obtained in this way have very good brilliance, fastness to rubbing, fastness to migration, fastness to heat, fastness to light and fastness to weathering.

We claim:

1. A pigmented organo macromolecular material comprising an organo macromolecular material and an azo pigment of the formula

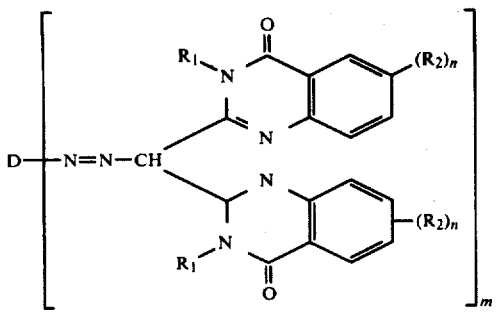

wherein

D is the radical of an aromatic or hetero-aromatic amine which is free from sulphonic acid groups;

m is the integer 1 or 2;

n denotes 0, 1, 2, 3 or 4;

$R_1$ is hydrogen or $C_1$-$C_4$ alkyl; and $R_2$ is chlorine, bromine, $Cl_1$-$C_4$-alkyl, $C_1$-$C_4$-alkoxy, nitro, trifluoromethyl, cyano, carboxamide, $C_1$-$C_4$-alkyl-carboxamide, phenylcarboxamide, $C_1$-$C_4$ alkylphenylcarboxamide, $C_1$-$C_4$-alkoxyphenylcarboxamide, fluoro-,chloro-, bromo-phenylcarboxamide, nitrophenylcarboxamide, benzylcarboxamide, $C_1$-$C_4$-alkylbenzylcarboxamide, $C_1$-$C_4$-alkoxybenzylcarboxamide, fluoro-,chloro-, bromobenzylcarboxamide, nitrobenzylcarboxamide, sulphonamide, $C_1$-$C_4$-alkylsulphonamide, phenylsulphonamide, $C_1$-$C_4$-alkylphenylsulphonamide, $C_1$-$C_4$-alkoxyphenylsulphonamide, fluoro-,chloro-, bromo-phenylsulphonamide, nitrophenylsulphonamide, benzylsulphonamide, $C_1$-$C_4$- alkylbenzylsulphonamide, $C_1$-$C_4$-akloxybenzylsulphonamide, fluoro-, chloro-, bromo-benzyl sulphonamide, nitrobenzylsulphonamide, $C_1$-$C_4$-alkylcarbonylamino, benzoylamino, chlorobenzoylamino, $C_1$-$C_4$-alkylbenzoylamino, $C_1$-$C_4$-alkoxybenzoylamino, nitrobenzoylamino, phenylamino, $C_1$-$C_4$-alkylphenylamino, $C_1$-$C_4$-alkoxyphenylamino, fluoro-, chloro-, bromophenylamino, or nitrophenylamino.

2. A pigmented organo macromolecular material according to claim 1, wherein said azo pigment has the formula

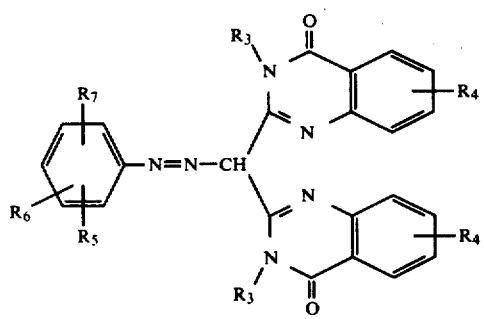

where $R_3$ is hydrogen or methyl;

$R_4$ is hydrogen, $C_1$-$C_4$ alkyl, $C_1$-$C_4$-alkoxy, halogen, nitro, $C_1$-$C_4$-alkylcarbonylamino, or $C_1$-$C_4$-alkylsulphonylamino;

$R_5$ is hydrogen, halogen, $C_1$-$C_4$-alkyl, $C_1$-$C_4$-alkoxy, nitro, cyano, $C_1$-$C_4$-alkylsulphonyl, trifluoromethyl, carboxamide, $C_1$-$C_4$-alkylcarboxamide, phenylcarboxamide, $C_1$-$C_4$-alkylphenylcarboxamide, $C_1$-$C_4$-alkoxyphenylcarboxamide, fluoro-, chloro-, bromo-phenylcarboxamide, nitrophenylcarboxamide, benzylcarboxamide, $C_1$-$C_4$-alkylbenzylcarboxamide, $C_1$-$C_4$-alkoxybenzylcarboxamide, fluoro-, chloro-, bromo-benzylcarboxamide, nitrobenzylcarboxamide, sulphonamide, $C_1$-$C_4$-alkylsulphonamide, phenylsulphonamide, $C_1$-$C_4$-alkylphenylsulphonamide, $C_1$-$C_4$-alkoxyphenylsulphonamide, fluoro-, chloro-, bromo-phenylsulphonamide, nitrophenylsulphonamide, benzylsulphonamide, $C_1$-$C_4$-alkylbenzylsulphonamide, $C_1$-$C_4$-alkoxybenzylsulphonamide, fluoro-, chloro-, bromo-benzylsulphonamide, nitrobenzylsulphonamide, $C_1$-$C_4$-alkylcarbonylamino, benzoylamino, chlorobenzoylamino, $C_1$-$C_4$-alkylbenzoylamino, $C_1$-$C_4$ alkoxybenzoylamino, nitrobenzoylamino, $C_1$-$C_4$-alkoxycarbonyl; $R_6$ is hydrogen, fluorine, chlorine, bromine, $C_1$-$C_4$-alkyl, cyano, $C_1$-$C_4$-alkoxy, nitro, or trifluoromethyl; and $R_7$ is hydrogen, chlorine, $C_1$-$C_4$-alkyl or $C_1$-$C_4$-alkoxy.

3. A pigmented organo macromolecular material according to claim 1, wherein said organo macromolecular material has the formula

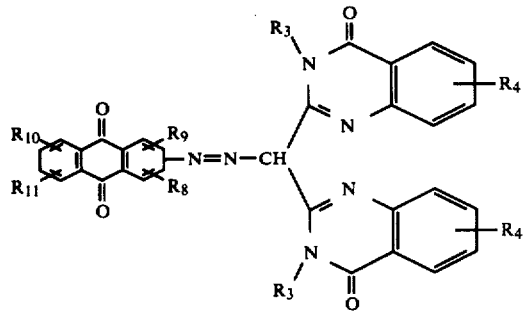

wherein $R_3$ is hydrogen or methyl;

$R_4$ is hydrogen, $C_1$-$C_4$-alkyl, $C_1$-$C_4$-alkoxy, fluorine, chlorine, bromine, nitro, $C_1$-$C_4$-alkylcarbonylamino, or $C_1$-$C_4$-alkylsulphonylamino; $R_8$ denotes hydrogen, fluorine, chlorine, bromine, nitro, $C_1$-$C_4$-alkyl, $C_1$-$C_4$-alkoxy, $C_1$-$C_4$-alkylamino, benzylamino, cyclohexylamino, $C_1$-$C_4$-alkylmercapto, phenylmercapto, $C_1$-$C_4$-alkylphenylmercapto, $C_1$-$C_4$-alkoxyphenylmercapto, fluoro-, chloro-,bromophenylmercapto, nitrophenylmercapto, carboxamide, mono- or di-$C_1$-$C_4$-alkylcarboxamide, mono- or di- phenylcarboxamide, mono- or di- $C_1$-$C_4$-alkylphenylcarboxamide, mono- or di- $C_1$-$C_4$-alkoxyphenylcarboxamide, mono- or di-fluoro, chloro, bromophenylcarboxamide, mono- or di-nitrophenylcarboxamide, mono- or di-benzylcarboxamide, $C_1$-$C_4$-alkylcarbonylamino, benzoylamino, chlorobenzoylamino, $C_1$-$C_4$-alkylbenzoylamino, $C_1$-$C_4$-alkoxybenzoylamino, nitrobenzoylamino, bromobenzoylamino, phenylamino, $C_1$-$C_4$-alkylphenylamino, $C_1$-$C_4$-alkoxyphenylamino, chlorophenylamino, nitrophenylamino, $C_1$-$C_4$ alkylsulphonylamino, phenylsulphonylamino , $C_1$-$C_4$-alkylphenylsulphonylamino, $C_1$-$C_4$-alkoxyphenylphenylsulphonylamino, fluoro-, chloro-, bromo-phenylsulphonylamino, or nitrophenylsulphonylamino, $C_1$–$C_4$-alkylcarbonyl, $C_1$–$C_4$-alkoxycarbonyl; $R_9$ is hydrogen, chlorine or hydroxyl; $R_{10}$ is hydrogen halogen, fluorine, chlorine, bromine, nitro, $C_1$–$C_4$-alkyl, $C_1$–$C_4$-alkoxy, $C_1$–$C_4$-alkoxycarbonyl, $C_1$–$C_4$-alkylcarbonyl, benzylamino, cyclohexylamino, $C_1$–$C_4$-alkylmercapto, phenylmercapto, $C_1$–$C_4$-alkylphenylmercapto, $C_1$–$C_4$-alkoxyphenylmercapto, fluoro-, chloro-, bromo-phenylmercapto, nitrophenylmercapto, carboxyl, hydroxy, carboxamide, mono- or di- $C_1$–$C_4$-alkylcarboxamide, mono- or di- phenylcarboxamide, mono- or di- $C_1$–$C_4$-alkylphenylcarboxamide, mono- or di- $C_1$–$C_4$-alkoxyphenylcarboxamide, mono- or di- fluoro-, chloro-, bromo-phenylcarboxamide, mono- or di- nitrophenyl carboxamide, mono- or di- benzylcarboxamide, $C_1$–$C_4$-alkylcarbonylamino, benzoylamino, chlorobenzoylamino, $C_1$–$C_4$-alkylbenzoylamino, $C_1$–$C_4$-alkoxybenzoylamino, nitrobenzoylamino, bromobenzoylamino, phenylamino, $C_1$–$C_4$-alkylphenylamino, $C_1$–$C_4$-alkoxyphenylamino, chlorophenylamino, bromophenylamino, nitrophenylamino, $C_1$–$C_4$-alkylsulphonylamino, phenylsulphonylamino, $C_1$–$C_4$-alkylphenylsulphonylamino, $C_1$–$C_4$-alkoxyphenylsulphonylamino, fluoro-, chloro-, bromo-phenylsulphonylamino, or nitrophenylsulphonylamino; and $R_{11}$ is hydrogen, fluorine, chlorine, bromine or hydroxyl.

4. A pigmented organo macromolecular material according to claim 1, wherein said azo pigment has the formula:

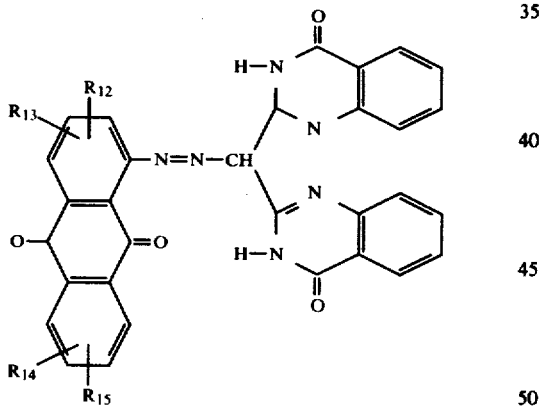

wherein $R_{12}$, $R_{13}$, $R_{14}$ and $R_{15}$ are hydrogen, chlorine, bromine, carboxyl, $C_1$–$C_4$-alkoxycarbonyl, carboxamide, $C_1$–$C_4$-alkylcarbonylamino, benzoylamino, mono- or di-nitrobenzoylamino, benzoylamino substituted with 1-5 chlorines or bromines, $C_1$–$C_4$-alkylsulphonylamino, phenylsulphonylamino, methylphenylsulphonylamino, methoxysulphonylamino, or chlorophenylsulphonylamino.

5. A pigmented organo macromolecular material according to claim 1, wherein said organo macromolecular material is polyacrylonitrile.

6. A spin dyed polyacrylonitrile, comprising polyacrylonitrile and an azo pigment of the formula

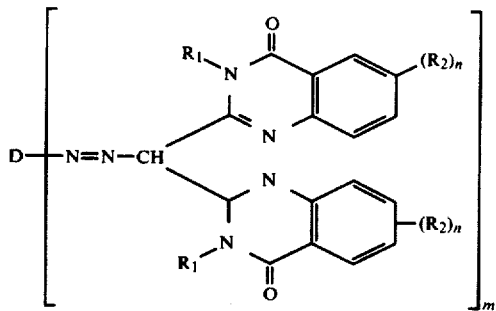

wherein

D is the radical of an aromatic or hetero-aromatic amine which is free from sulphonic acid groups;

m is the integer 1 or 2;

n denotes 0, 1, 2, 3 or 4;

$R_1$ is hydrogen or $C_1$–$C_4$ alkyl; and $R_2$ is chlorine, bromine, $Cl_1$–$C_4$-alkyl, $C_1$–$C_4$-alkoxy, nitro, trifluoromethyl, cyano, carboxamide, $C_1$–$C_4$-alkyl-carboxamide, phenylcarboxamide, $C_1$–$C_4$-alkylphenylcarboxamide, $C_1$–$C_4$-alkoxyphenylcarboxamide, fluoro-, chloro-, bromo-phenylcarboxamide, nitrophenylcarboxamide, benzylcarboxamide, $C_1$–$C_4$-alkylbenzylcarboxamide, $C_1$–$C_4$-alkoxybenzylcarboxamide, fluoro-, chloro-, bromo-benzylcarboxamide, nitrobenzylcarboxamide, sulphonamide, $C_1$–$C_4$-alkylsulphonamide, phenylsulphonamide, $C_1$–$C_4$-alkylphenylsulphonamide, $C_1$–$C_4$-alkoxyphenylsulphonamide, fluoro-, chloro-, bromo-phenylsulphonamide, nitrophenylsulphonamide, benzylsulphonamide, $C_1$–$C_4$-alkylbenzylsulphonamide, $C_1$–$C_4$-alkoxybenzylsulphonamide, fluoro-, chloro-, bromo-benzyl sulphonamide, nitrobenzylsulphonamide, $C_1$–$C_4$-alkylcarbonylamino, benzoylamino, chlorobenzoylamino, $C_1$–$C_4$-alkylbenzoylamino, $C_1$–$C_4$-alkoxybenzoylamino, nitrobenzoylamino, phenylamino, $C_1$–$C_4$-alkylphenylamino, $C_1$–$C_4$-alkoxyphenylamino, fluoro-, chloro-, bromophenylamino, or nitrophenylamino.

* * * * *